United States Patent
Peeters et al.

(10) Patent No.: US 10,441,219 B2
(45) Date of Patent: Oct. 15, 2019

(54) MULTI-STATE CLIP-ON FIXATION METHOD FOR PULSE OXIMETER

(71) Applicant: KONINKLIJKE PHILIPS N.V., Eindhoven (NL)

(72) Inventors: Wouter Herman Peeters, Waalre (NL); Egbertus Reinier Jacobs, Overloon (NL); Rick Bezemer, Amsterdam (NL); Jens Muehlsteff, Aachen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 169 days.

(21) Appl. No.: 15/551,720

(22) PCT Filed: Feb. 23, 2016

(86) PCT No.: PCT/IB2016/050951
§ 371 (c)(1),
(2) Date: Aug. 17, 2017

(87) PCT Pub. No.: WO2016/135617
PCT Pub. Date: Sep. 1, 2016

(65) Prior Publication Data
US 2019/0117159 A1    Apr. 25, 2019

Related U.S. Application Data

(60) Provisional application No. 62/119,461, filed on Feb. 23, 2015.

(51) Int. Cl.
*A61B 5/1455* (2006.01)
*A61B 5/00* (2006.01)
*A61B 5/024* (2006.01)

(52) U.S. Cl.
CPC ........ *A61B 5/6838* (2013.01); *A61B 5/02427* (2013.01); *A61B 5/02438* (2013.01);
(Continued)

(58) Field of Classification Search
CPC . A61B 5/6838; A61B 5/1455; A61B 5/14551; A61B 5/14552; A61B 5/02427;
(Continued)

(56) References Cited

U.S. PATENT DOCUMENTS 6,115,621 A * 9/2000 Chin .................. A61B 5/14552
600/323
8,073,518 B2   12/2011 Chin
(Continued)

FOREIGN PATENT DOCUMENTS

| JP | H0657316 | 3/1994 |
| JP | H07155311 | 6/1995 |
| JP | 2004194908 | 7/2004 |

*Primary Examiner* — Eric F Winakur
*Assistant Examiner* — Chu Chuan Liu

(57) ABSTRACT

A device (10, 10', 10") includes a light source (12) and a light detector (14) spaced from, and in communication with, the light source (12). An electronic processor (18) is programmed to compute pulse oximetry data from output of the light detector (14). A clamping member (26) is included, on or in which the light source (12) and the light detector (14) are disposed. The clamping member (26) is configured for attachment to a human body part with the body part disposed between the light source (12) and the light detector (14) such that light from the light source (12) passes through the body part to reach the light detector (14). The clamping member (26) is configured to attach to the body part by transitioning from a first stable state to a second stable state via a compression force applied to the clamping member (26).

6 Claims, 7 Drawing Sheets

Open stable state

(52) U.S. Cl.
CPC ........ *A61B 5/14552* (2013.01); *A61B 5/6816* (2013.01); *A61B 5/6819* (2013.01); *A61B 5/0002* (2013.01); *A61B 5/6826* (2013.01); *A61B 5/6843* (2013.01)

(58) Field of Classification Search
CPC . A61B 5/6816; A61B 5/6819; A61B 5/02438; A61B 5/6826; A61B 5/6843
See application file for complete search history.

(56) References Cited

U.S. PATENT DOCUMENTS

| | | |
|---|---|---|
| 2004/0049207 A1 | 3/2004 | Goldfarb |
| 2005/0075550 A1 | 4/2005 | Lindekugel |
| 2007/0032712 A1 | 2/2007 | Raridan |
| 2007/0032716 A1 | 2/2007 | Raridan |
| 2007/0078317 A1 | 4/2007 | Matlock |
| 2009/0171224 A1* | 7/2009 | Jochim .............. A61B 5/14552 600/501 |
| 2009/0275813 A1 | 11/2009 | Davis |
| 2010/0081900 A1 | 4/2010 | Price |
| 2011/0032473 A1 | 2/2011 | Medana |
| 2014/0005557 A1 | 1/2014 | Rich |
| 2014/0014789 A1 | 1/2014 | Verma |
| 2014/0155713 A1 | 6/2014 | Melker |

* cited by examiner

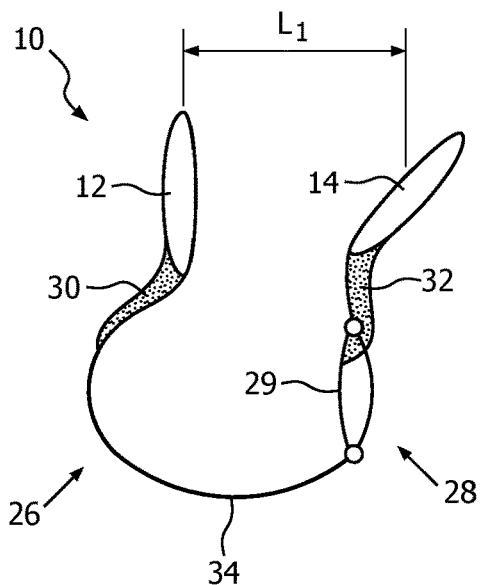
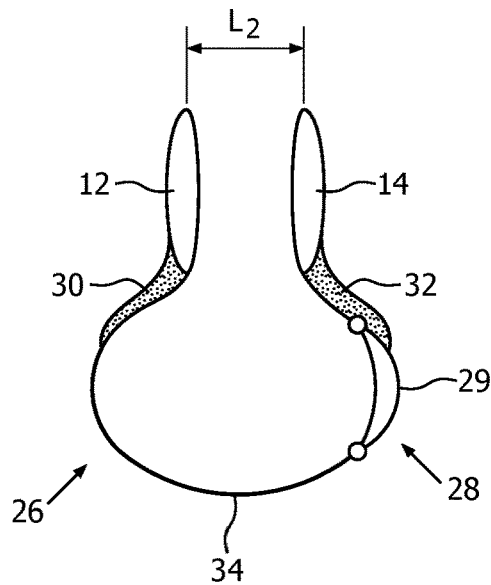
Open stable state
FIG. 2A
Closed stable state
FIG. 2D
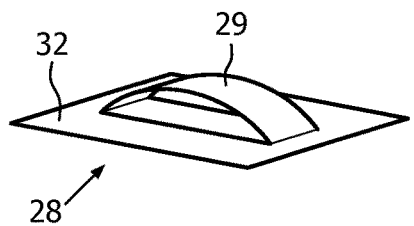
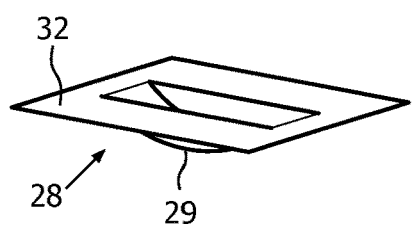
Open stable state
FIG. 2B
Closed stable state
FIG. 2E
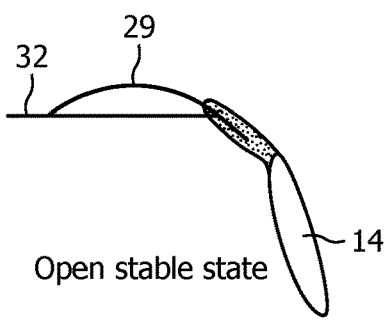
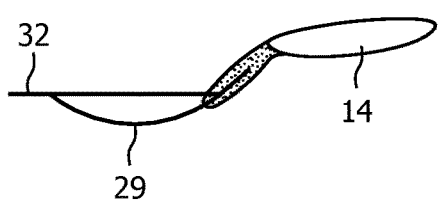
Open stable state
FIG. 2C
Closed stable state
FIG. 2F

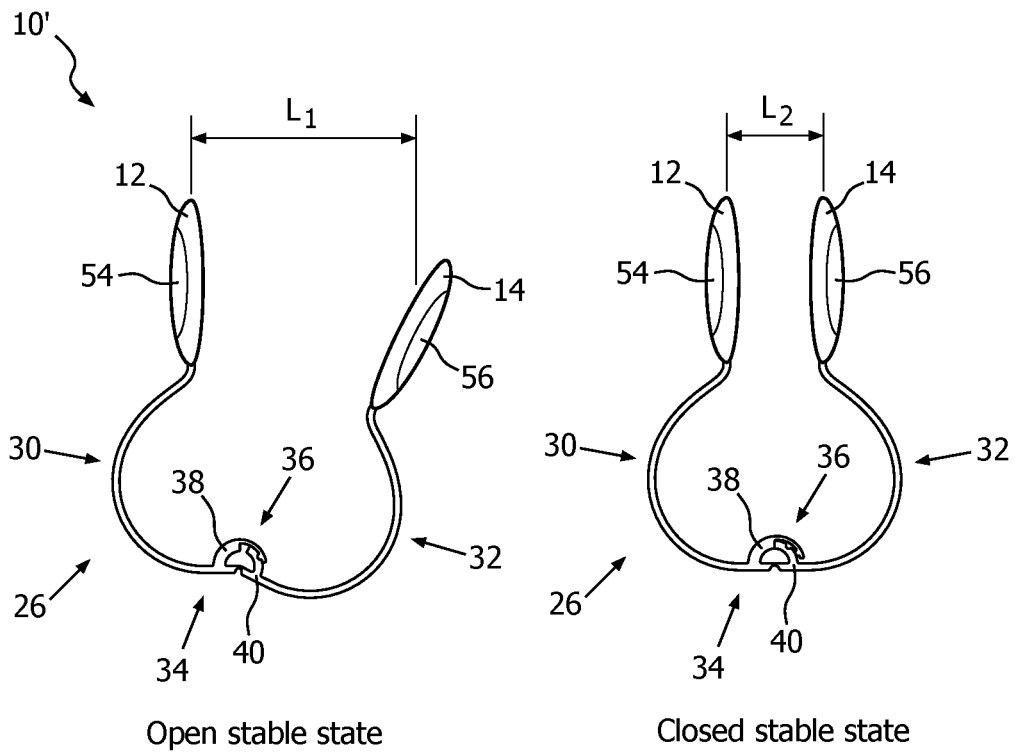
Open stable state
FIG. 3A
Closed stable state
FIG. 3C
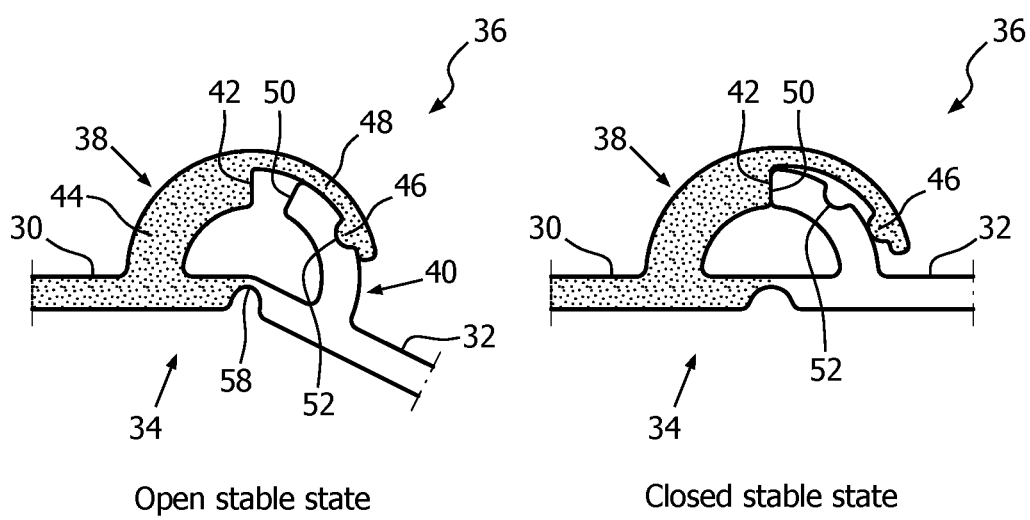
Open stable state
FIG. 3B
Closed stable state
FIG. 3D

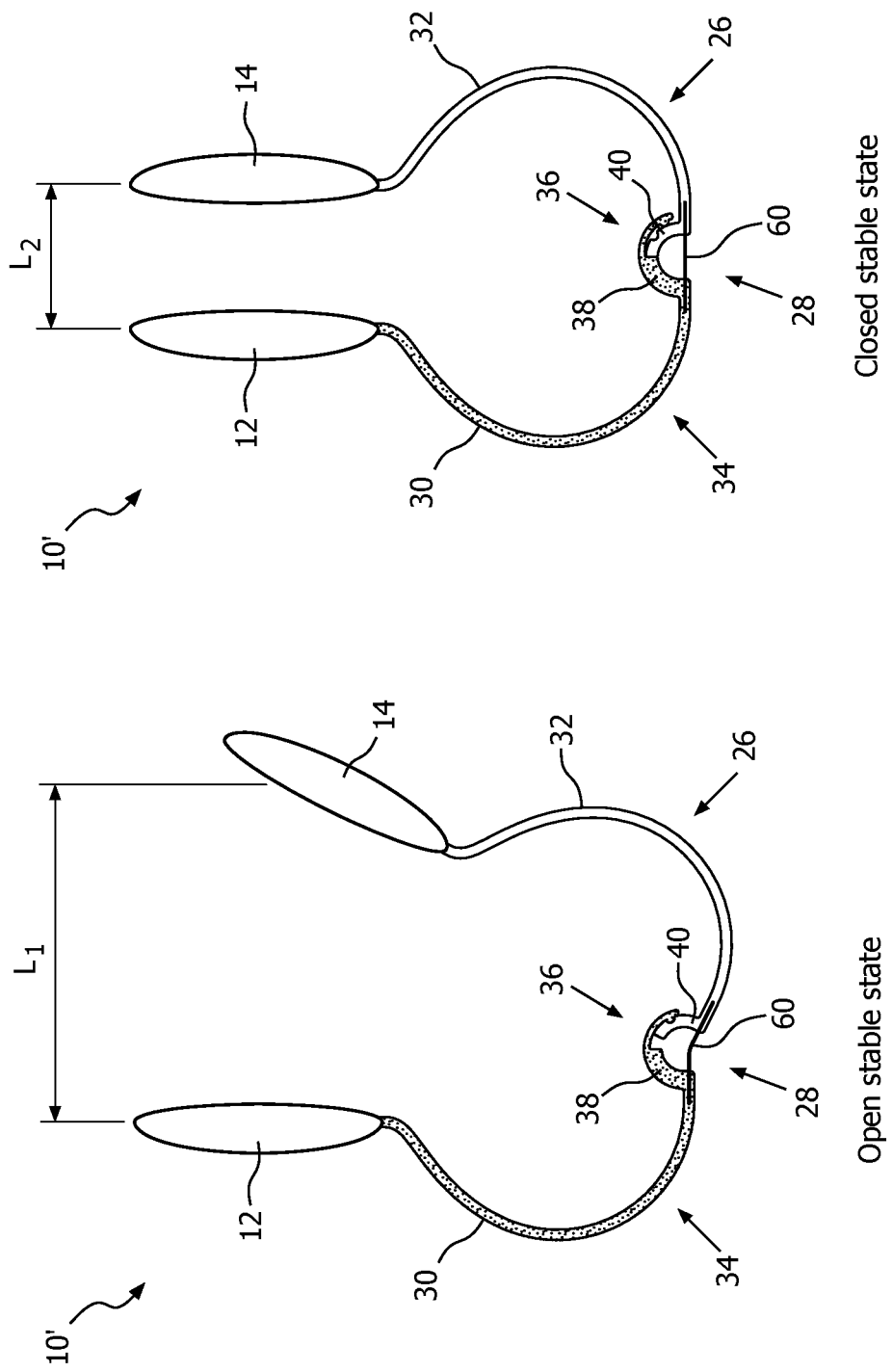

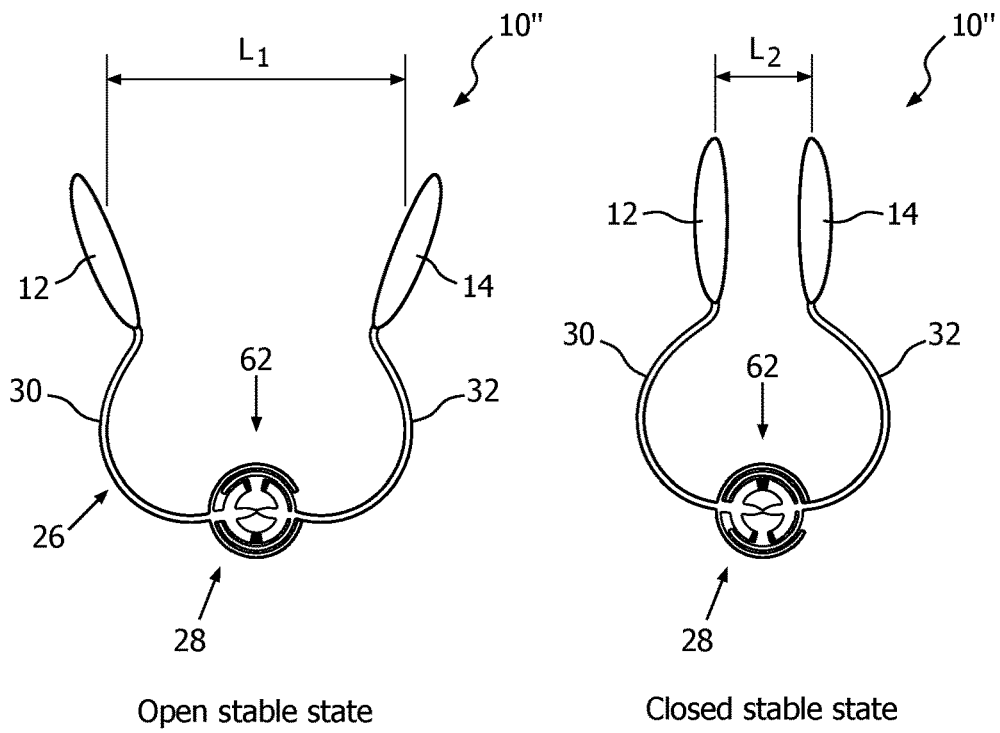
Open stable state
FIG. 4A
Closed stable state
FIG. 4B
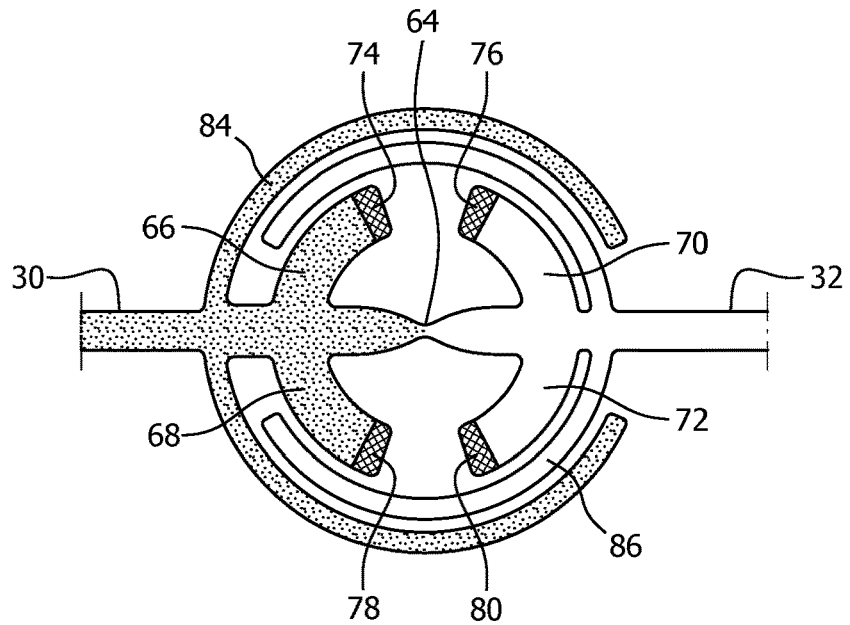
FIG. 4C

Closed stable state

Open stable state

MULTI-STATE CLIP-ON FIXATION METHOD FOR PULSE OXIMETER

CROSS REFERENCE TO RELATED APPLICATIONS

This application is the U.S. National Phase application under 35 U.S.C. § 371 of International Application No. PCT/IB2016/050951, filed Feb. 23, 2016, published as WO 2016/135617 on Sep. 1, 2016, which claims the benefit of U.S. Provisional Patent Application No. 62/119,461 filed on Feb. 23, 2015. These applications are hereby incorporated by reference herein.

FIELD

The following relates generally to measuring indications of pulse rate and arterial oxygen saturation ($SpO_2$) of a patient. It finds particular application in conjunction with a pulse oximeter of the "clip-on" type in which the pulse oximeter clips onto a finger, earlobe, or so forth. However, it is to be understood that it also finds application in other usage scenarios and is not necessarily limited to the aforementioned application.

BACKGROUND

Pulse oximetry has become a standard of care in clinical practice. It provides a continuous non-invasive readout of critically important information about the patient's pulse rate and $SpO_2$.

In pulse oximetry, red and infrared light is passed through the tissue and is picked up by a light detector. The cardiac pulse rate is derived from a pulsatile light signal that is caused by the pulsating arterial blood volume. A measurement of oxygenation is made based on the ratio of pulse amplitudes at red and infrared signals, based on the difference in color between oxygen-bound hemoglobin and oxygen-unbound hemoglobin.

Typically, pulse oximeters are attached to the human body with various clip mechanisms. In one example, a "compression-handle mechanism" or "clothespin mechanism" is used, in which the pulse oximeter consists of a spring or flexible material under tension. The user opens the clip mechanism by compressing a handle (e.g., like a clothes peg), positioning the sensor on the patient, and releasing the compression force on the handle. Compression-handle mechanisms can be used on a target location of a patient (e.g. a finger, an ear lobe, an alar wing, and the like). The compression handles, however, can be heavy and bulky. As a result, such compression-handle mechanisms are restricted to larger body parts (e.g., fingers, ears, and the like) and cannot be used on smaller body parts (e.g., an alar wing and the like).

In another example, the clip mechanism can include an adhesive-wrap mechanism, where an adhesive sensor is wrapped onto a target tissue and fixated with an extra adhesive or a hook-and-loop fastener. Adhesive-wrap mechanisms can be used on a target location of a patient (e.g. a finger, a forehead, and the like).

In a further example, a clip mechanism with a flexible structure that deforms when attached to a target tissue. The flexible structure does not use a compression handle. Flexible structures can be used on a target location of a patient (e.g., an ear concha, a finger, and the like).

Other designs include a compression handle mechanism in which a removable compression handle is used to apply the pulse oximeter to a target location, and then the applicator is removed. To later remove the pulse oximeter from the patient, the applicator is reattached before the sensor can be removed.

The following provides new and improved methods and systems which overcome the above-referenced problems and others.

BRIEF SUMMARY

It is recognized herein that existing pulse oximeter designs have certain deficiencies. The "clip on" design has the potential to pinch the finger, earlobe, or other target location, which can cause pain and lead to tissue necrosis. For example, the devices can fully close and pinch the patient, thereby causing pain and discomfort to the patient. Designs including an applicator are complex two-piece components that can be difficult to manipulate, and the applicator is a separable component. As a result, the applicator can often become lost and thus unavailable when a nurse needs it to remove the sensor from the patient. If an applicator is unavailable when the nurse or other medical person is removing the pulse oximeter, there is a temptation to remove it without using an applicator, which can be uncomfortable for the patient. In addition, the sensor can be clamped incorrectly (i.e., loosely) on the patient, and fall off during use.

Various improvements are disclosed herein.

In some illustrative embodiments disclosed herein, a mechanism is provided in which the pulse oximeter can be in a stable open or closed state. In the open state, the pulse oximeter can easily be placed over the target location (e.g., the alar wing, the ear lobe, and the like). When the pulse oximeter is positioned on the target tissue, an optical source of the pulse oximeter is disposed on one side of the target tissue, and the detector is disposed on an opposing second side of the target tissue. When the sensor is properly positioned, a user applies a compression force on the two parts of the pulse oximeter such that it transitions into a closed state. In the closed state, the separation of the detector part and the source part is decreased such that fixation of the sensor is ensured (i.e., it will not fall off). By lifting either the detector or the source, the pulse oximeter can transition into its open state, after which it can be removed from the target tissue. The mechanism does not include a compression handle, which allows the sensor to be made much smaller and lighter for attachment to small spaces (e.g., the alar wing) while increasing patient comfort. In addition, the mechanism does not easily fall off without a force applied thereto. The mechanism also does not include a separable applicator, thereby increasing the ease of attachment to the patient.

In the closed state, the source and detector each exert a limited compression force on the target location to prevent necrosis and pain. To achieve this, the resulting separation between the source and detector part in the closed-state in one example is larger than zero (i.e., not fully closed). In another example, the separation between the source and the detector in the closed-state is zero (i.e., the source and the detector contact each other). To accomplish this, various mechanisms that can be included with the pulse oximeter (e.g., using magnets, leaf springs, hinges, mechanical stops and the like).

In accordance with one aspect, a pulse oximeter includes a light source and a light detector spaced from, and in communication with, the light source. An electronic processor is programmed to compute pulse oximetry data from output of the light detector. A clamping member is included, on or in which the light source and the light detector are disposed. The clamping member is configured for attachment to a human body part with the body part disposed between the light source and the light detector such that light from the light source passes through the body part to reach the light detector. The clamping member is configured to attach to the body part by transitioning from a first stable state to a second stable state via a compression force applied to the clamping member.

In accordance with another aspect, a pulse oximeter includes a light source, a light detector, and a clamping member. The clamping member includes a first end portion that supports the light source. A second end portion supports the light detector. A bi-stable hinge connects the first end portion and the second end portion. The bi-stable hinge has, in the absence of anything being disposed between the light source and the light detector: (i) an open stable state in which the light source and the light detector are spaced apart by an open state gap; and (ii) a closed stable state in which the light source and the light detector are spaced apart by a closed state gap that is non-zero or zero, and that is smaller than the open state gap.

In accordance with another aspect, a pulse oximeter for measuring oxygen saturation in a target is provided. The pulse oximeter includes a clamping member configured for at least partial attachment to a portion of the target. The clamping member is configured for transition from a first stable state to a second stable state via a compression force applied thereto. The compression force is applied by an actuating member.

One advantage resides in placement of a pulse oximeter without the need for a removable component.

Another advantage resides in a pulse oximeter transitionable between a stable open state and a stable closed state.

Another advantage resides in increased patient comfort in a closed state of the device.

Another advantage resides in a smaller and lighter pulse oximeter for attachment to a small space on a patient.

Still further advantages of the present invention will be appreciated to those of ordinary skill in the art upon reading and understand the following detailed description.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

FIGS. 2A-F are cross-sectional perspective views of a first embodiment the device of FIG. 1;

FIGS. 3A-F are cross-sectional perspective views of a second embodiment the device of FIG. 1;

FIGS. 4A-E are cross-sectional perspective views of a third embodiment the device of FIG. 1.

DETAILED DESCRIPTION

Figure 1:
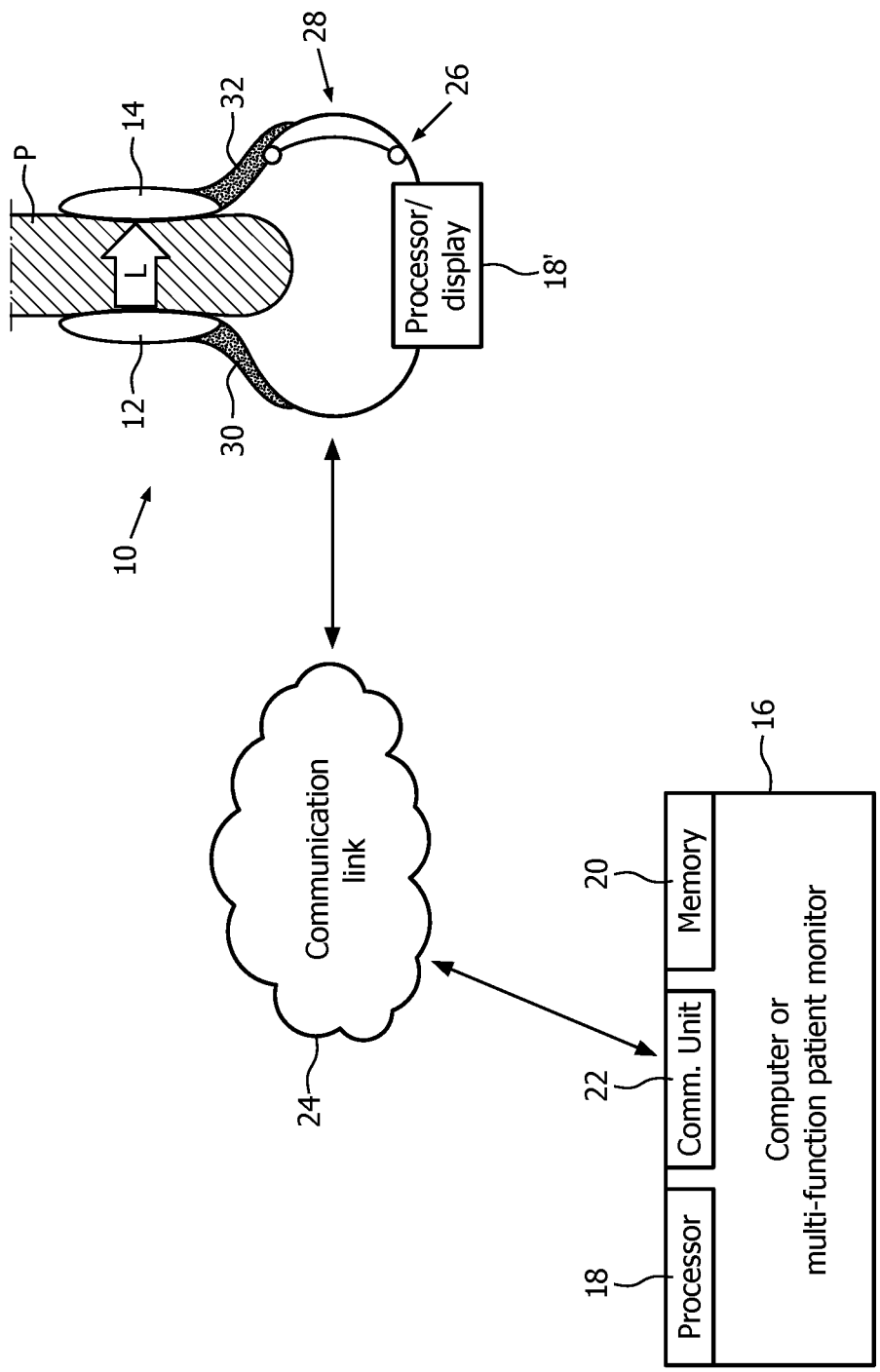
FIG. 1 illustrates a device in communication with one or more processors in one embodiment of the present disclosure.

It is recognized herein that existing pulse oximeter designs have certain deficiencies. The "clip on" design has the potential to pinch the finger, earlobe, or other target location, which can cause pain and lead to tissue necrosis (e.g., by fully closing and thus pinching the patient). Designs including an applicator are complex two-piece devices that can be difficult to manipulate, and the applicator is a disposable component, which can often be lost or misplaced. If an applicator is unavailable when the nurse or other medical person is removing the pulse oximeter, there is a temptation to remove the pulse oximeter without using an applicator, which can be uncomfortable for the patient. In addition, the sensor can be clamped loosely on the patient, and thus fall off during use Pulse oximeters disclosed herein comprise a clamping member with a bi-stable hinge that is transitionable between a stable open state and a stable closed state. With reference to FIG. 1, the device 10 includes a light source 12 and a light detector 14 that are clamped onto a body part P, such as an earlobe, finger, infant's foot, alar wing, or so forth, so that each is positioned on, or adjacent to, the target tissue P. The body part P is generally a human body part, although it is contemplated to employ the device in a veterinary setting in which case the body part may be of an animal. The body part comprises target tissue carrying or perfused with blood whose oxygenation is to be assessed. As used herein, the term "target tissue" refers to any desired target tissue (e.g., tissue of a body part P such as an alar wing, a finger, an ear lobe, a forehead, an ear concha, a septum, inside a nostril, behind the ear, inside the ear, an area above the eye brow, in the eye pit, inside the esophagus, the oral mucosal, the skull, on the forehead, etc.) of a patient. As described herein, the device 10 is a pulse oximeter for measuring oxygen saturation in a patient. However, it will be appreciated that the device 10 can be any suitable device to measure of physiological characteristic of a patient (e.g., a photoplethymography sensor, a perfusion device, a device to measure more than one wavelength, and the like). To this end, a clamping member 26 includes a first end portion 30 supporting the light source 12 and a second end portion 32 supporting the light detector 14. The optical components 12, 14 may be variously mounted on or in the respective end portions 30, 32, for example being embedded into housings integrally formed in the end portions 30, 32, mounted on facing surfaces of the end portions 30, 32, or so forth. Any such housings or mountings may optionally include spacers, offsets, or so forth. As used herein, the optical components 12, 14 include their respective housings, spacers, or the like, so that the light source 12 and detector 14 can be considered as physical units that contact/press onto the body part P. The clamping member 26 further includes a bi-stable hinge 28 connecting the first end portion 30 and the second end portion 32. The clamping member 26 allows the light source 12 and light detector 14 to be clamped onto a body part P, such as an earlobe, with the body part P disposed between the light source 12 and the light detector 14. Light L generated by the light source 12 passes though the body part P and is detected after transmission by the light detector 14. The illustrative pulse oximeter 10 thus operates in a transmission mode.

The output of the light detector 14 is processed to generate pulse oximetry data. In some embodiments, the pulse oximeter 10 is in communication with a computer, multi-function patient monitor, or other electronic data processing device 16 that includes one or more processors (or units, or electronics) 18 executing computer executable instructions that are stored on one or more memories 20 associated with the one or more processors 18. It is, however, contemplated that at least some of the data processing functionality can be implemented in hardware without the use of processors. For example, analog circuitry can be employed. Further, the electronic data processing device 16 includes a communication interface 22 communicating with the pulse oximeter 10 via a communication link 24 (e.g., a wireless communication link such as a Bluetooth or Zigbee link, a wired communication link via a physical cable, or the like). In one example, the pulse oximeter 10 is mechanically connected (e.g., with a cable) to the computer 16. In another example, the pulse oximeter 10 is electronically connected (e.g., over a wireless network) to the computer 16. Stated another way, the light source 12 and the light detector 14 are in communication with the processors 18. In other embodiments, a processor 18' is integral with the pulse oximeter 10 (e.g. mounted on or in the clamping member 26 in the diagrammatic illustrative example). In this case, the unit 18' may include an on-board display, e.g. an LCD display, to show the oximetry data. It will be appreciated that the pulse oximeter 10 may be viewed as including only the optical components 12, 14 and associated mounting hardware 26, or may be viewed as further including the electronics 18 or 18'.

The processors 18, 18' are programmed to compute oximetry data generated from the output of the light detector 14 which detects light L from the light source 12 after transmission through the body part P. Optical pulse oximetry is a well-known technique, one approach of which is described briefly in the following. In this example, the light source 12 is configured to emit red light and infrared light. In one example, the light source 12 can include at least one pair of LEDs (not shown) with a first LED configured to emit red light, and a second LED configured to emit infrared light. In another example, the light source 12 is a single broadband source (e.g. a phosphorized UV LED) with band pass optical filters to pass red and infrared light.

The light detector 14 is configured to absorb the emitted red and infrared light from the light source 12 after transmission through the body part P. The absorption of the emitted red and infrared light from the light source 12 differs significantly between blood containing oxygen and blood lacking oxygen. Oxygenated hemoglobin in the target tissue P absorbs more infrared light and allows more red light to pass through. Deoxygenated hemoglobin, on the other hand, allows more infrared light to pass through and absorbs more red light. The light detector 14 responds to the red light and infrared light separately. The transmitted red and infrared light intensities are measured, and separate normalized signals are produced for each wavelength by the processors 18. By subtracting the minimum transmitted light from the peak transmitted light in each wavelength over the cardiac cycle, the effects of other tissues is corrected for. The ratio of the red light measurement to the infrared light measurement (which represents the ratio of oxygenated hemoglobin to deoxygenated hemoglobin) is then calculated by the processor 18. This ratio is then converted to $SpO_2$ by the processor 18 via a lookup table stored within the computer 16 (e.g., in the memories 20). Optionally, the pulse oximetry data also includes a pulse rate (i.e. heart rate) which is derived from the periodicity of the red and infrared signals. This is merely an illustrative example, and other pulse oximetry optical configurations and associated data processing algorithms are also contemplated. The pulse oximetry data (e.g. $SpO_2$ and optional heart rate) are suitably displayed on a display of the computer or patient monitor 16 as a numerical value that is updated on a real-time basis, and/or plotted as a trendline, or is displayed on an on-board LCD display in embodiments with self-contained electronics 18'.

In the pulse oximetry embodiments disclosed herein, the clamping member 26 includes the bi-stable hinge 28. The hinge 28 has, in the absence of anything being disposed between the light source 12 and the light detector 14, the following stable states: (i) an open stable state in which the light source 12 and the light detector 14 are spaced apart by an open state gap; and (ii) a closed stable state in which the light source 12 and the light detector 14 are spaced apart by a closed state gap that is non-zero and that is smaller than the open state gap. This differs from a conventional clip-on pulse oximeter that is spring-biased to a closed position, and does not have a closed stable state with a non-zero gap. Rather, a typical clip-on pulse oximeter is biased fully closed, so that the light source and light detector have a zero gap, i.e., contact each other, when nothing is disposed between the light source and detector. As a result, a conventional clip-on pulse oximeter when clamped onto a body part exerts substantial, and generally uncontrolled, clamp force on the body part, which can lead to physical discomfort and, over time, can produce physical effects such as bruising or tissue necrosis. In some examples, the clamping member 26 can have a closed stable state in which the light source 12 and the light detector 14 are spaced apart by a closed state gap that is zero while the hinge 28 does not apply an uncomfortable force to the patient.

In the following, some illustrative examples of some pulse oximeters with suitable clamping members incorporating various bi-stable hinge configurations are described.

With reference to FIGS. 2A-F, the pulse oximeter 10 of one embodiment includes the light source 12, the light detector 14, a clamping member 26, and a biasing member or a bi-stable hinge 28. As shown, the clamping member 26 generally has a U-shaped configuration; however, other shapes are possible (e.g., circular, square, trapezoidal, n-polygonal, and the like). The clamping member 26 is sized and dimensioned (e.g., surface area, thickness, and the like) to allow the device 10 to be attached to the target tissue without causing discomfort to the patient. The clamping member 26 can be made from any suitable material (e.g., a hard plastic, a soft plastic, a thin metal, an elastomer (i.e., silicone), and the like). Advantageously, the clamping member 26 includes the bi-stable hinge 28, thereby allowing the clamping member 26 to support the light source 12 and the light detector 14 while simultaneously allowing the clamping member 26 to transition from a first (i.e. open) stable state to a second (i.e. closed) stable state, as described in more detail below.

The clamping member 26 includes a first end portion 30, a second end portion 32 spaced from the first end portion 30, and an intermediary portion 34 including the hinge 28 disposed therebetween. As shown, the light source 12 is attached to the clamping member 26 at the first end portion 30, and the light source 14 is attached to the clamping member 26 at the second end portion 32. However, it will be appreciated that the light source 12 can be attached at the second end portion 32 and the light detector 14 can be attached at the first end portion 30.

The clamping member 26 is configured for attachment to a portion of the target tissue. For example, the clamping member 26 is configured for transition from a first stable state to a second stable state when a compression force is applied thereto. The compression force can be applied in any known manner (e.g., pushing with a finger, pushing with another object, pinching, and the like). For example, a finger can be pressed against a leaf spring 29 of the first illustrative hinge 28 to apply the compression force to cause the clamping member 26 to transition from the first stable state to the second stable state. Transitioning to the closed state can for example also be achieved by applying an external biasing force to the source 12 and detector 14. The hinge 28 is disposed on a portion of the clamping member 26. As shown, a first end portion of the hinge 28 is disposed on the second end portion 32 and a second end portion of the hinge 28 is disposed on the intermediary portion 34 (which in turn connects with the first end portion 30). A length of the leaf spring 29 is longer than the distance at points on the second end portion 32 and the intermediary portion 34 to which the leaf spring 29 is attached.

In the embodiment shown in FIGS. 2A-F, the hinge 28 includes a leaf spring member 29 configured to apply the compression force to the clamping member 26. The spring member 29 is bendable in lateral directions, and it is neither compressible nor stretchable along a longitudinal axis thereof. The unconstrained shape of the spring member 29 is flat (i.e., such that an energetically lowest state thereof is a flat state). The spring member 29 is moveable between an unlocked position in which the spring is arced in a first direction, and a locked position in which the spring is arced in an opposite second direction.

As shown in FIGS. 2A-C, the clamping member 26 is shown in a first stable state. The first stable state of the clamping member 26 provides an open configuration for the clamping member 26—hence, the first stable state of the hinge 28 is also referred to as the "open" stable state of the hinge 28. In the open configuration, the spring member 29 is in an unlocked position. In the unlocked position, the spring member 29 is disposed within the interior area of the U-shaped configuration of the clamping member 26. When the spring member 29 is in the unlocked position (i.e. open stable state), the second end portion 32 of the clamping member 26 is moveable relative to the first end portion 30 thereof. Stated another way, the second end portion 32 is laterally offset from the spring member (i.e., in a "right" direction). Consequently, the light detector 14 is spaced from the light source 12 is at a first distance $L_1$. Since this is the open configuration, the first distance $L_1$ is also referred to herein as the "open state gap" $L_1$. When the clamping member 26 is in the open configuration, the pulse oximeter 10 is positioned on, or over, the target tissue. To this end, in the open configuration the light source 12 and the light detector 14 are sufficiently spaced to allow the target tissue to fit therebetween.

The second stable state of the clamping member 26 is shown in FIGS. 2D-F. The second stable state of the clamping member 26 provides a closed configuration for the clamping member 26—hence, the second stable state of the hinge 28 is also referred to as the "closed" stable state of the hinge 28. In the closed configuration, the spring member 29 is in a locked position. For example, in the locked position, the spring member 29 has been laterally moved (for example, by pushing or pulling) so that the leaf spring member 29 is disposed outside of the interior area of the U-shaped configuration of the clamping member 26. When the spring member 29 is in the locked position (i.e. closed stable state), the second end portion 32 of the clamping member 26 is fixed relative to the first end portion 30 thereof (in the absence of anything being disposed in-between). Stated another way, the second end portion 32 is laterally offset from the spring member 28 (i.e., in a "left" direction). Consequently, the light detector 14 is spaced from the light source 12 is at a second distance $L_2$ that is non-zero (or zero), but is less than the first distance $L_1$. Since this is the closed configuration, the second distance $L_2$ is also referred to herein as the "closed state gap" $L_2$. When the clamping member 26 is in the closed configuration, the device 10 is clamped to the target tissue disposed between the optical components 12, 14. For example, the light source 12 and the light detector 14 are sufficiently positioned relative to each other to connect the device 10 to the target tissue without causing discomfort to the user.

The second distance $L_2$ is obtained if nothing is disposed between the light source 12 and the detector 14. In actual use, the body part P will be placed in the gap before switching from the open stable state to the closed stable state. The separation $L_2$ is chosen so that it is just slightly smaller than the expected thickness of the body part P, so that some clamping force is applied, but less than would be applied if a conventional spring-loaded clip was used. To provide some clamping force, the illustrative clamping member 26 includes at least one flexible member that accommodates the body part P by flexing when the hinge 28 is in the closed stable state to allow the gap between the light source 12 and the light detector 14 to be larger than the closed state gap $L_2$ in the absence of anything being disposed between the light source 12 and the light detector 14. The at least one flexible member may, for example, include one or more of the first end portion 30, the second end portion 32, and/or the intermediary portion 34.

Advantageously, each of the open and closed configurations is a stable state. In the illustrative example of FIG. 2, the leaf spring 28 is arced in a first direction in the first (open) stable state (FIGS. 2A, 2B, and 2C), and is arced in an opposite second direction in the second (closed) stable state (FIGS. 2D, 2E, and 2F). The stable states are stable in that the hinge 28 stays in the stable state unless and until a compression force is applied to transition to the other stable state. Once the device 10 is affixed to the target tissue, it cannot come loose or be removed without moving the spring member 28 from the locked position to the unlocked position. For example, in the locked position, an overlapping connection between the spring member 28 and the light detector 14 is rigid such that any rotation or movement of the light detector 14 causes deformation of the spring member 28. In the closed configuration, a resulting tissue force is determined by: (1) the thickness of the target tissue, (2) the closed state gap or separation $L_2$ of the light source 12 and the light detector 14 in the absence of anything being disposed in the gap, and (3) the stiffness (i.e. flexibility) of the whole device (e.g., based on the geometry and material thereof). Consequently, the device 10 reduces this resulting tissue force.

In the embodiment of FIG. 2, the bi-stable hinge 28 is provided with bi-stability by the leaf spring 29 which has two stable states defined by the leaf spring being arced in one of two possible, and opposite, arc directions. This can be seen by comparing FIGS. 2A-2C with FIGS. 2D-2F. In other designs, the bi-stable hinge 28 includes the following components: a first mechanical stop that is engaged in the open stable state; a second mechanical stop that is engaged in the closed stable state; and a biasing element (e.g. a spring or sets of magnets) configured to respond to disengagement of the first mechanical stop by rotating the hinge to engage the second mechanical stop to place the bi-stable hinge into the closed stable state. In some such embodiments, the biasing element is further configured to respond to disengagement of the second mechanical stop by rotating the hinge to engage the first mechanical stop to place the bi-stable hinge into the open stable state. Some illustrative examples of hinges of this general design are presented in the following.

FIGS. 3A-F show an alternative embodiment of a device 10'. For conciseness, repeated descriptions of elements common to the device 10 and the device 10' will be omitted. The device 10' includes the light source 12, the light detector 14, the clamping member 26, and a bi-stable hinge 36 which replaces the bi-stable hinge 28 of the previous embodiment.

As shown, the bi-stable hinge 36 is centrally located on the intermediary portion 34 of the clamping member 26. However, it will be appreciated that the hinge 36 can be disposed on any suitable portion of the clamping member 26 (e.g., adjacent the first or second end portion 30 or 32).

The bi-stable hinge 36 includes a first component 38 and a second component 40 configured to interact with the first component 38. The first component 38 includes a first hard stop 42 connected to the intermediary portion 34 at a first end portion 44 of the first component 38, and a protrusion 46 disposed at a second end portion 48 of the first component 38. In some examples, the first component 38 has a tapered configuration such that the second end portion 48 thereof tapers from the first end portion 44 thereof. The second component 40 includes a second hard stop 50 adapted to engage the first hard stop 42, and a notch 52 adapted to receive the protrusion 46. These features collectively define: (i) a first mechanical stop comprising the protrusion 46 and mating notch 52; and (ii) a second mechanical stop comprising the hard stops 42, 50. A hinged region 58 disposed on a portion of the intermediary portion 34 interconnects the first and second components 38 and 40.

As shown in FIGS. 3A-D, the bi-stable hinge 28 further comprises a biasing element in the form of a first magnet 54 disposed on the light source 12, and a second magnet 56 disposed on the light detector 14. The first and second magnets 54 and 56 are configured to be attracted to each other to apply the compression force to the clamping member 26, as described in more detail below. In one alternative example, the first and second magnets 54 and 56 are integrated into the hinge 36. In another alternative example, the first and second magnets 54 and 56 are disposed on the opposing sides of the hinge 36 on the intermediary portion 34. It is also possible to replace one of the magnets 54 or 56 with a non-magnetized ferromagnetic mass.

In a variant embodiment, as shown in FIGS. 3E-F, the first and second mechanical stops have the same configuration as in the embodiment of FIGS. 3A-D, but the biasing element comprises a spring member 60 (e.g., a leaf spring, a compression spring, a tension spring, a coil spring, and the like) that interconnects, and is operably embedded within portions of each of, the first and second components 38 and 40. The spring member 60 is tensioned to apply the compression force to the clamping member 26, as described in more detail below.

In FIGS. 3A, 3B, and 3E, the clamping member 26 is shown in the first stable state (i.e., the open configuration). In the open configuration, the hinge 36 is in an unlocked position. For example, in the unlocked position, the first and second hard stops 42 and 50 are spaced from each other, and the protrusion 46 is received in the notch 52. When the hinge 36 is in the unlocked position, the second end portion 32 of the clamping member 26 is moveable relative to the first end portion 30 thereof. Consequently, the light detector 14 is spaced from the light source 12 is at the first distance $L_1$. When the clamping member 26 is in the open configuration, the device 10 is positioned on or within the target tissue.

In FIGS. 3C, 3D, and 3F, the clamping member 26 is shown in the second stable state (i.e., the closed configuration). In the closed configuration, the hinge 36 is in a locked position. In one example, in the locked position, the second end portion 32 has been rotated (for example, by pushing or pulling), until the first and second magnets 54 and 56 are magnetically attracted to each other to lock the clamping member 26. The first and second magnets 54 and 56 cooperate to apply the compression force to the clamping member 26, thereby preventing further movement of the second end portion 30 of the clamping member 26. In another example, in the locked position, the second end portion 32 has been rotated (for example, by pushing or pulling), until the spring member 60 tensions to apply the compression force to the clamping member 26, thereby preventing further movement of the second end portion 30 of the clamping member 26. As a result, the second component 40 rotatably moves such that the protrusion 48 is disengaged with, and thus spaced from, the notch 54, thereby allowing the first and second hard stops 42 and 50 to abut each other. When the hinge 36 is in the locked position, the second end portion 32 of the clamping member 26 is fixed relative to the first end portion 30 thereof. Consequently, the light detector 14 is spaced from the light source 12 is at the second distance $L_2$. When the clamping member 26 is in the closed configuration, the device 10 is clamped to the target tissue. For example, the light source 12 and the light detector 14 are drawn towards each other to connect the device 10 to the target tissue without causing discomfort to the user.

In the embodiment of FIGS. 3A-3D, the biasing element 54, 56 provides only single-directional bias. In other words, the magnets 54, 56 are attracted to each other in order to respond to disengagement of the first mechanical stop 46, 52 by rotating the hinge 36 to engage the second mechanical stop 42, 50 to place the bi-stable hinge 36 into the closed stable state, but the magnets 54, 56 do not operate in the opposite direction—indeed, to the contrary the user must pull apart the ends 12, 14 against the attractive force of the magnets 54, 56 to disengage the second mechanical stop 42, 50 and continue pulling apart until the first stop 46, 52 engages to hold the ends open against the magnetic force. On the other hand, the leaf spring 60 of the embodiment of FIGS. 3E-F operates similarly to the leaf spring 29 of the embodiment of FIG. 2 in order to respond to disengagement of the second mechanical stop 42, 50 by rotating the hinge 36 to engage the first mechanical stop 46, 52 to place the bi-stable hinge into the open stable state.

FIGS. 4A-E show another embodiment of the device 10″ which employs first and second mechanical stops in combination with a biasing element. For conciseness, repeated descriptions of elements common to the device 10, the device 10′, and/or the device 10″ will be omitted. The device 10″ includes the light source 12, the light detector 14, the clamping member 26, and a bi-stable hinge 62. As shown, the hinge 62 is centrally located on the intermediary portion 34 of the clamping member 26. However, it will be appreciated that the hinge 62 can be disposed on any suitable portion of the clamping member 26 (e.g., adjacent the first or second end portion 30 or 32).

Figure 4E:
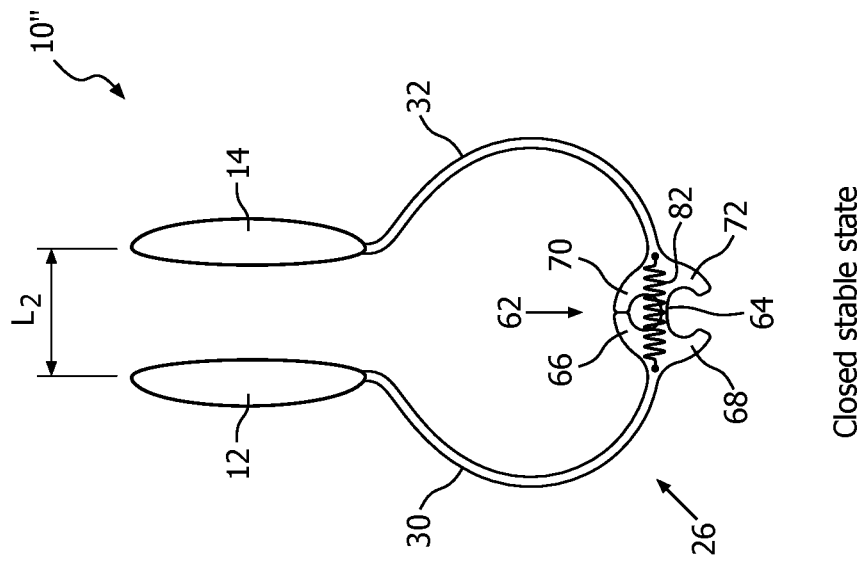
Figure 4D:
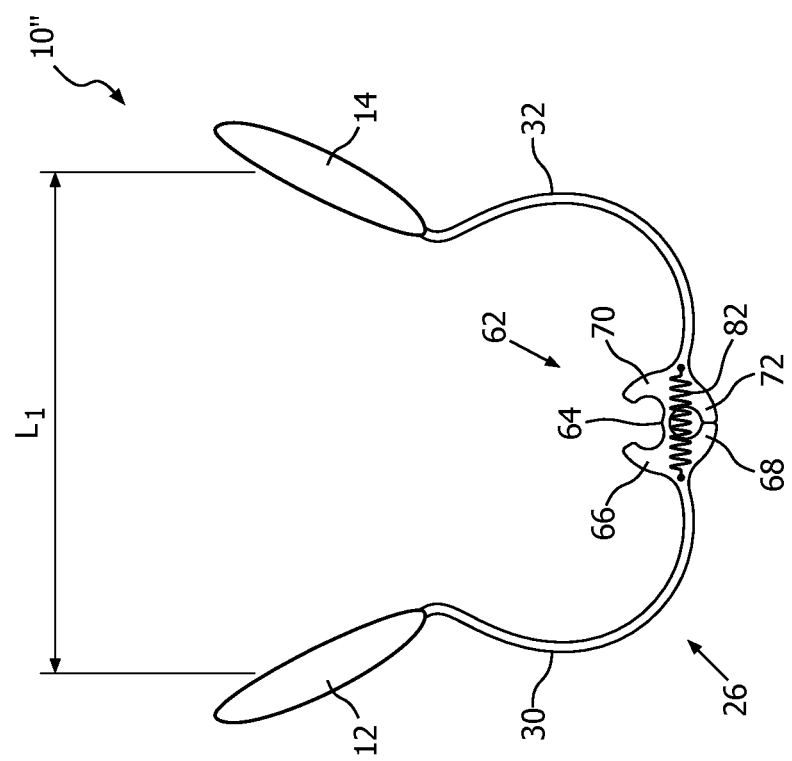

The hinge 62 includes a hinged connection 64 that interconnects the first end portion 30 of the clamping member 26 and the second end portion 32 thereof. Disposed on a first side of the hinged connection 64 (e.g., a "left" side) are a first abutment member 66 disposed on a first side of the first end portion 30 (i.e., the interior area defined by the clamping member 26) and a second abutment member 68 disposed on the opposing side of the first end portion 30 (i.e., "exterior" to the clamping member 26). Disposed on a second side of the hinge 62 (e.g., a "right" side) are a third abutment member 70 diametrically opposed from the first abutment member 62 relative to the hinged connection 64, and a fourth abutment member 72 diametrically opposed from the second abutment member 68 relative to the hinged connection 64. In some instances, the first and third abutment members 66 and 70 are selectively engaged with each other, and the second and fourth abutment members 68 and 72 are selectively engaged with each other. These features collectively define: (i) a first mechanical stop comprising the abutment members 68, 72; and (ii) a second mechanical stop comprising the abutment members 66, 70. The clamping member 26 is in the open configuration when the second and fourth abutment members 68 and 72 are engaged with each other (that is, when the first mechanical stop 68, 72 is engaged), and the clamping member 26 is in the closed configuration when the first and third abutment members 66 and 70 are engaged with each other (that is, when the second mechanical stop 66, 70 is engaged). In one example embodiment, as shown in FIGS. 4A-C, a biasing element includes first, second, third, and fourth magnets, 74, 76, 78, and 80 disposed on a corresponding one of the first, second, third, and fourth abutment members 66, 68, 70, and 72. In another example embodiment, as shown in FIGS. 4D-E, the biasing element includes a spring member 82 (e.g., a leaf spring, a compression spring, a tension spring, a coil spring, and the like) interconnects, and is operably embedded within portions of each of, the first and second end portions 30 and 32. The spring member 82 is tensioned to apply the compression force F to the clamping member 26. Stated another way, the spring member 82 is operably engaged with each of the first, second, third, and fourth abutment members 66, 68, 70, and 72.

The device 10", as shown in FIGS. 4A-C operates substantially similarly to the device 10' shown in FIGS. 3A-D. In an unlocked position of the hinge 62, the second and fourth abutment members 68 and 72 are engaged with each other when the clamping member 26 is in the open configuration, thereby providing an expansion force on the clamping member 26. The clamping member 26 maintains the open configuration until the compression force is applied to the hinge 62 upon movement of the second end portion 32 of the clamping device 26. As a result, in a locked position of the hinge 62 the second and fourth abutment members 68 and 72 are disengaged with each other, and the first and third abutment members 66 and 70 are engaged with each other.

In addition, the device 10", as shown in FIGS. 4D-E operates in a substantially similar manner to the embodiment shown in FIGS. 4A-C, in which the spring member 82 is tensioned to allow the second and fourth abutment members 68 and 72 to engage with each other when the clamping member 26 is in the open configuration, thereby providing an expansion force on the clamping member 26. The clamping member 26 maintains the open configuration until the compression force is applied to the hinge 62 by the spring member 82 upon movement of the second end portion 32 of the clamping device 26. As a result, in a locked position of the hinge 62 the second and fourth abutment members 68 and 72 are disengaged with each other, and the first and third abutment members 66 and 70 are engaged with each other.

In the embodiments of FIGS. 4A-C, the biasing element provides bi-directional force, i.e. magnets 74, 76 operate to close the clamping member 26 when the first mechanical stop 68, 72 is disengaged; while magnets 78, 80 operate to open the clamping member 26 when the second mechanical stop 66, 70 is disengaged. The operation here depends upon the fact that the magnetic force decreases with increasing separation of the magnets, so that the magnet pair with smallest separation "wins". Such bi-directional force is also provided by the embodiment of FIGS. 4D-E because the force applied by the spring 82 reverses in direction when the centerline of the spring 82 crosses the hinged connection or pivot point 64.

In some examples, as shown in FIG. 4C, the hinge 62 can include a first cover member 84 connected to the first end portion 30 of the clamping member 26, and a second cover member 86 connected to the second end portion 32 thereof. Advantageously, the first and second cover members 84 and 86 prevent portions of the target tissue from entering the hinge 62 upon attachment of the device 10" thereto, thereby increasing the comfort of the patient while decreasing the chances of target tissue getting caught within the hinge 62. In other words, the covers block the hinge 62 from pinching the tissue. As shown in FIG. 4C, the second cover member 84 substantially surround the first, second, third and fourth abutment members 66, 68, 70, and 72, and the first cover member 82 substantially surrounds the second cover member 84. It will be appreciated that the first cover member 82 can surround the abutment members 66, 68, 70, and 72, and the second cover member 84 can surround the first cover member 82.

Figure 5:
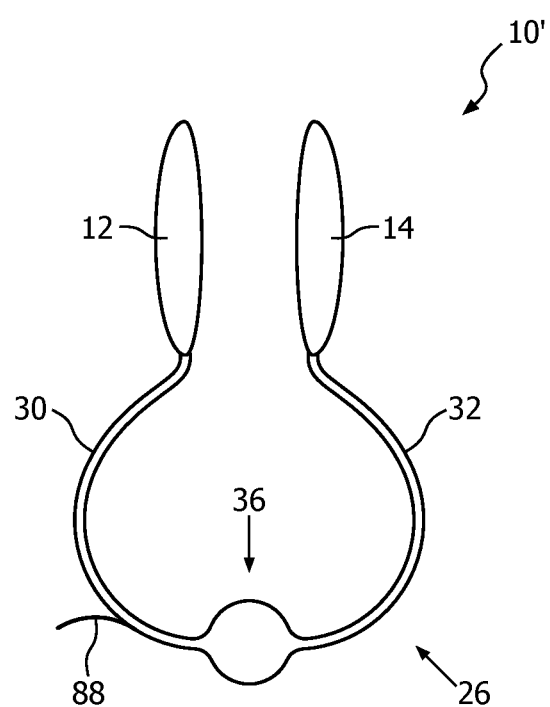
FIG. 5 is a perspective view of a fourth embodiment the device of FIG. 1.

In some embodiments, as shown in FIG. 5, the device 10, 10', and/or 10" can include a handle 88 connected to a portion of the clamping member 26 (e.g., the intermediary portion 34). The handle 88 is ergonomic to help a user transition the clamping member 26 from the first stable state (i.e., the open configuration) to the second stable state (i.e., the closed configuration). Advantageously, the handle 88 has a shape that follows the contour of a finger, thereby allowing a user to easily apply a force thereto to rotate the second end portion 32 relative to the first end portion 30 without a risk of the user's fingers slipping off the handle 88. In some examples, the handle 88 is provided when the device 10, 10', and/or 10" is located on a difficult target tissue. e.g., a part of the alar wing sensor inside the nose of the subject). The handle 88 allows a user to easily attach the device 10, 10', and/or 10" to the target tissue.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:
1. A device including:
a light source;
a light detector spaced from, and in communication with, the light source;
an electronic processor programmed to compute pulse oximetry data from output of the light detector;
a clamping member on or in which the light source and the light detector are disposed, the clamping member configured for attachment to a human body part with the body part disposed between the light source and the light detector such that light from the light source passes through the body part to reach the light detector;
a bi-stable hinge configured to apply a compression force to the clamping member, thereby allowing the clamping member to transition from a first stable state to a second stable state,
wherein the bi-stable hinge includes a leaf spring configured to apply the compression force to the clamping member, the leaf spring being movable between an unlocked position in which the leaf spring is arced in a first direction and a locked position in which the leaf spring is arced in an opposite second direction,
wherein the clamping member is configured to attach to the body part by transitioning from the first stable state to the second stable state via the compression force applied to the clamping member.

2. The device according to claim 1, wherein the first stable state of the clamping member includes an open configuration and the second stable state of the clamping member includes a closed configuration in which there is a minimum gap between the light source and the light detector.

3. The device according to claim 1, wherein, when the leaf spring is in the unlocked position, the clamping member is in the first stable state and, when the leaf spring is in the locked position, the clamping member is in the second stable state.

4. The device according to claim 3, wherein, when the leaf spring member is in the unlocked position, the light detector is at a first distance ($L_1$) from the light source and, when the leaf spring is in the locked position, the light detector is at a second distance ($L_2$) from the light source that is less than the first distance.

5. The device according to claim 4, wherein $L_2$ is zero and $L_1$ is greater than zero.

6. The device according to claim 1, wherein the device is a pulse oximeter.

\* \* \* \* \*